United States Patent [19]
November

[11] 4,216,673
[45] Aug. 12, 1980

[54] FLUID PROPERTY DETECTION SYSTEM
[75] Inventor: Milton H. November, Hacienda Heights, Calif.
[73] Assignee: International Telephone and Telegraph Corporation, New York, N.Y.
[21] Appl. No.: 10,058
[22] Filed: Feb. 7, 1979
[51] Int. Cl.³ .............................................. G01F 1/76
[52] U.S. Cl. ..................... 73/861; 73/195; 73/861.03
[58] Field of Search ............. 73/194 M, 195, 202, 73/205 D, 231 M, 32 R

[56] References Cited
U.S. PATENT DOCUMENTS
| | | | |
|---|---|---|---|
| 2,772,567 | 12/1956 | Boden et al. | 73/194 |
| 3,430,489 | 3/1969 | Pfrehm | 73/231 |

*Primary Examiner*—Herbert Goldstein
*Attorney, Agent, or Firm*—A. Donald Stolzy

[57] ABSTRACT

A differential pressure Δp is detected across an orifice plate in a pipe section. The same differential pressure is also allowed to drive a turbine meter. The turbine meter is conventional and produces electrical output pulses at a frequency $f_1$ proportional to the volume flow rate therethrough. It then has been found that the properties of a fluid in the pipe section and in the turbine meter may be found automatically by electronic computation of first and second ratios $$\Delta p/f_1$$

and $$\Delta p/f_1^2$$

respectively, where the first and second ratios are proportional to mass flow rate of the fluid in the pipe section or total mass flow when the mass flow rate is integrated with respect to real time, and the density of the fluid respectively.

9 Claims, 3 Drawing Figures

FLUID PROPERTY DETECTION SYSTEM

BACKGROUND OF THE INVENTION

This invention relates to analog and/or digital apparatus for producing outputs proportional to one or more properties of a fluid, and more particularly to density and/or mass flow rate and/or total mass flow instruments.

PRIOR ART STATEMENT

It is old in the art to connect a differential pressure unit (DPU) across an orifice in a pipe section to determine the volume flow rate of a fluid in the pipe section. However, the flow rate so determined may be inaccurate if the fluid density varies with time.

It is also old in the art to connect a turbine flowmeter across an orifice plate without benefit of a DPU.

SUMMARY OF THE INVENTION

In accordance with the system of the present invention, the above-described and other disadvantages of the prior art are overcome by combining a DPU and a turbine meter to derive mass flow rate or total mass flow or density of any combination of or all of these three properties, individually, alternately or simultaneously.

BRIEF DESCRIPTION OF THE DRAWINGS

In the accompanying drawings which illustrate exemplary embodiments of the present invention.

DESCRIPTION OF THE PREFERRED EMBODIMENT

Figure 1:
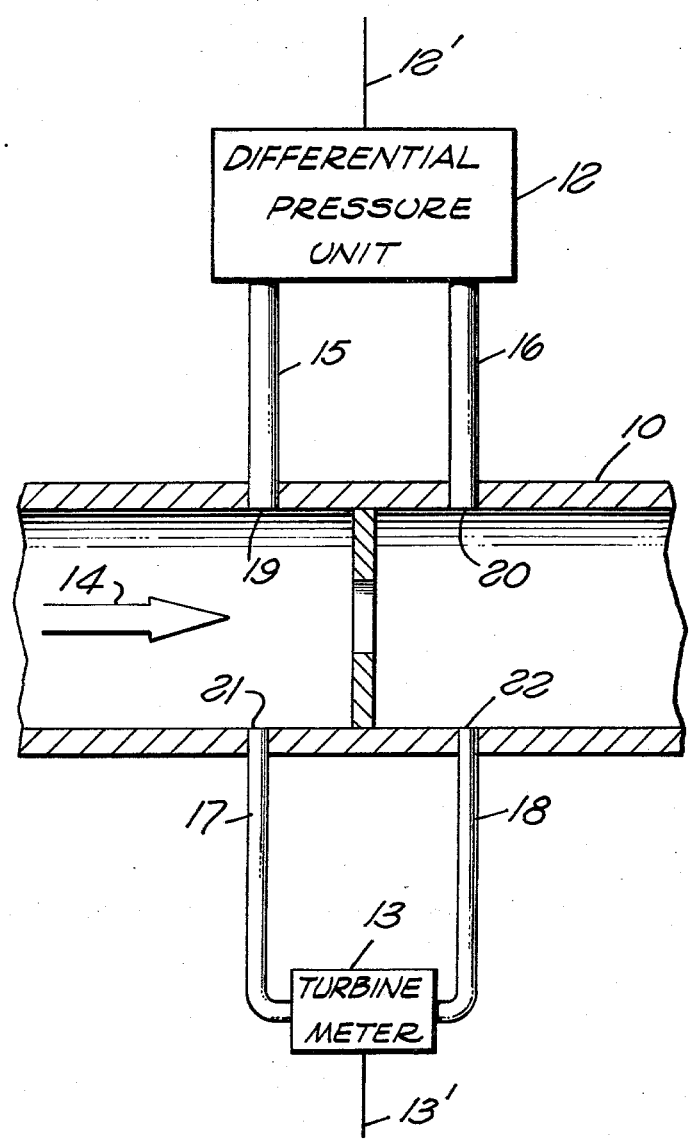
FIG. 1 is a diagrammatic view of a portion of the structures employed in accordance with present invention.

In the drawings, in FIG. 1, a pipe section 10 is shown having an orifice plate 11 fixed therein. A conventional DPU 12 is connected across orifice plate 11. DPU 12 produces an analog voltage or current proportional to the difference $\Delta p$ between the pressures in tubes 15 and 16 via an output lead 12'. Similarly, a turbine meter 13 is also connected across orifice plate 11. Turbine meter 13 produces pulses on an output lead 13' of a pulse repetition frequency $f_1$ proportional to the volume flow rate therethrough. A flow can be in either direction inside pipe section 10; however, if it is in the direction of an arrow 14, hollow tubes 15, 16 and 17 are inlet tubes, and tube 18 is an outlet tube. All of the tubes 15–18 have hollow interiors in communication with the fluid filled interior of pipe section 10 through ends 19, 20, 21 and 22 that open into the interior of pipe section 10.

The embodiments of the present invention show in FIGS. 2 and 3 operates as follows:

It is known that the square of the volume rate of flow $V_o^2$ through pipe section 10 can be defined by $$V_o^2 = \frac{2K_o g \Delta p}{d} \tag{1}$$

where $K_o$ is a constant, g is acceleration due to gravity, and d is the density of the fluid in pipe section 10.

It is also known that the square of the volume rate of flow $V_1^2$ through turbine meter inlet and outlet tubes 17 and 18, respectively is $$V_1^2 = \frac{2K_1 g \Delta p}{d} \tag{2}$$

where $K_1$ in another constant.

Hence, $$\frac{V_1^2}{K_1} = \frac{V_o^2}{K_o} \tag{3}$$

and $$V_1 = [V_o]\left[\frac{K_1}{K_o}\right]^{\frac{1}{2}} \tag{4}$$

As stated previously, it is also known that $$f_1 = K_2 V_1 \tag{5}$$

where $K_2$ is a constant.

Thus $$f_1 = [K_2 V_o]\left[\frac{K_1}{K_o}\right]^{\frac{1}{2}} \tag{6}$$

Solving (1) for $\Delta p$ $$\Delta p = \frac{d V_o^2}{2g K_o} \tag{7}$$

Thus, from (6) and (7)

$$\frac{\Delta p}{f_1} = \left[\frac{d V_o^2}{2g K_o}\right]\left[\frac{(K_o)^{\frac{1}{2}}}{(K_2 V_o)(K_1)^{\frac{1}{2}}}\right] \tag{8}$$

$$\frac{\Delta p}{f_1} = 0\, K_3 \dot{m} \tag{9}$$

where $$K_3 = \frac{(K_o K_1)^{-\frac{1}{2}}}{2g K_2} \tag{10}$$

$$\dot{m} = d V_o \tag{11}$$

and $\dot{m}$ is the mass flow rate.

In other words, the ratio $$\frac{\Delta p}{f_1} \tag{12}$$

is directly proportional to the mass flow rate within pipe section 10.

As will be seen, the ratio (12) can be converted to groups of pulses, and if these pulses are counted, the total count will be directly proportional to the total mass flow.

Using (8)

$$\frac{\Delta p}{f_1^2} = \left[\frac{dV_o^2}{2gK_o}\right]\left[\frac{K_o}{K_2^2 V_o^2 K_1}\right] \qquad (13)$$

$$\frac{\Delta p}{f_1^2} = K_4 d \qquad (14)$$

where $$K_4 = \frac{1}{2gK_2^2 K_1} \qquad (15)$$

Thus, the ratio $$\frac{\Delta p}{f_1^2} \qquad (16)$$

is directly proportional to the density d of the fluid.

THE EMBODIMENT OF FIG. 2

Figure 2:
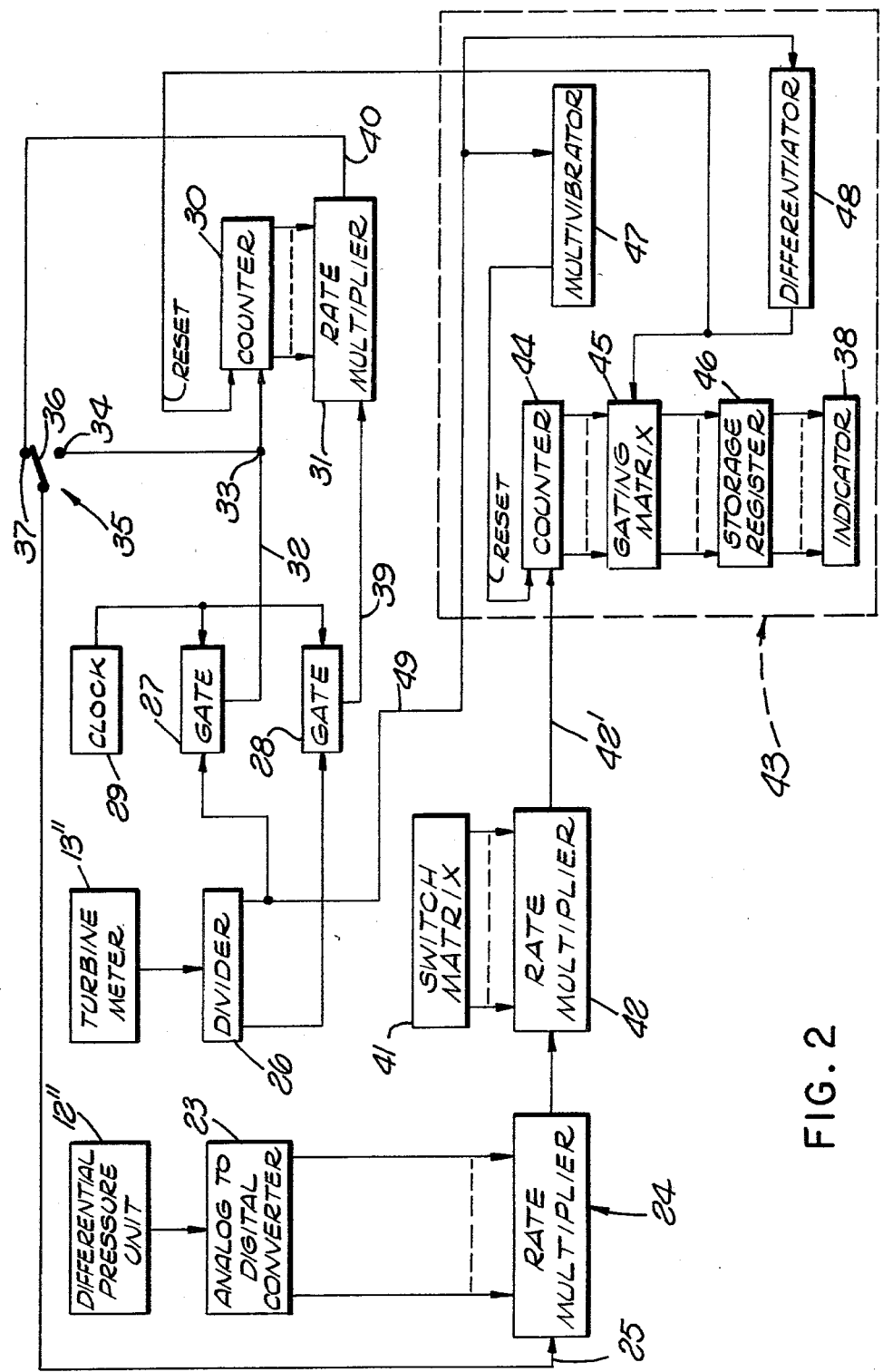
FIG. 2 is a block diagram of one embodiment of the present invention.

A DPU 12″ in FIG. 2 corresponds to DPU 12 in FIG. 1. A turbine meter 13″ in FIG. 2 corresponds to turbine meter 13 in FIG. 1.

In FIG. 2 an analog-to-digital converter (ADC) 23 is connected from DPU 12″ to a rate multiplier 24 to multiply the corresponding digital number times the pulses appearing on lead 25.

Turbine meter 13″ operates a divider 26 which opens gates 27 and 28 alternately and allows pulses from a clock 29 to pass to a counter 30 and a rate multiplier 31, respectively.

Gate 27 has an output lead 32 connected through a junction 33 to counter 30 and to a contact 34 of a switch 35. Switch 35 is a single-pole, double-throw switch having a pole 36 and a contact 37 connected from the output of rate multiplier 31 over a lead 40. Pole 36 is connected to input lead 25 of rate multiplier 24.

The embodiment of FIG. 2 operates alternatively to indicate mass flow rate or density. When switch 35 is in the position shown an indicator 38 registers density. When switch 35 in the position not shown, indicator 38 will register mass flow rate.

The number of pulses passing gate 27 is proportional to the period $T_1$ of $f_1$
where $$T_1 = \frac{1}{f_1} \qquad (17)$$

Hence $$\frac{\Delta p}{f_1^2} \qquad (18)$$

is computed by $$T_1^2 \Delta p \qquad (19)$$

where the stored count in register 30 is proportional to $T_1$ and the number of pulses on lead 39 is also proportional to $T_1$. Thus output lead 40 of rate multiplier 31 is thus proportional to $T_1^2$. These pulses are multiplied by a number proportional to $\Delta p$ by rate multiplier 24.

A switch matrix 41 must normally be manually set according to the position of switch 35. The system of FIG. 2 may be calibrated for each position of switch 35 empirically by the use of matrix 41, if desired. Matrix 41 merely applies the proper constant (e.g. proportional to $K_4$) so that indicator 38 will read properly in conventional units of mass per unit time or mass per unit volume for the positions of switch 35 not shown and shown, respectively.

An output circuit 43 contains a counter 44, a gating matrix 45, a storage register 46 and indicator 38 connected in succession from the output of rate multiplier 42. Output circuit 43 may be entirely conventional. Any counter updating circuit may be used therefore. A multivibrator (MV) 47 resets counter 44 slightly after the output pulse of a differentiator 48. Differentiator 48 operates sampling matrix 45 and the reset of counter 30. Both MV 47 and differentiator 48 are operated over a lead 49.

OPERATION OF THE EMBODIMENT OF FIG. 2

To cause indicator 38 to indicate density, switch 35 is thrown to the position shown. Counter 30 registers a value proportional to $T_1$. The output of gate 28 is a number of pulses also proportional to $T_1$. The output of rate multiplier 31 is then proportional to $T_1^2$. The outputs of rate multipliers 24 and 42, with switch matrix 41 set to cause indicator 38 to read in mass per unit volume, are proportional to $T_1^2\Delta p$ because of the $\Delta p$ input from converter 23.

Since $$T_1 = \frac{1}{f_1} \qquad (20)$$

the outputs of rate multipliers 24 and 42 are proportional to $$\frac{\Delta p}{f_1^2} \qquad (21)$$

where $$\frac{\Delta p}{f_1^2} = K_4 d \qquad (22)$$

see equation (14), and the outputs of rate multipliers 24 and 42 are proportional to the density of the fluid flowing in pipe section 10 (FIG. 1).

Figure 3:
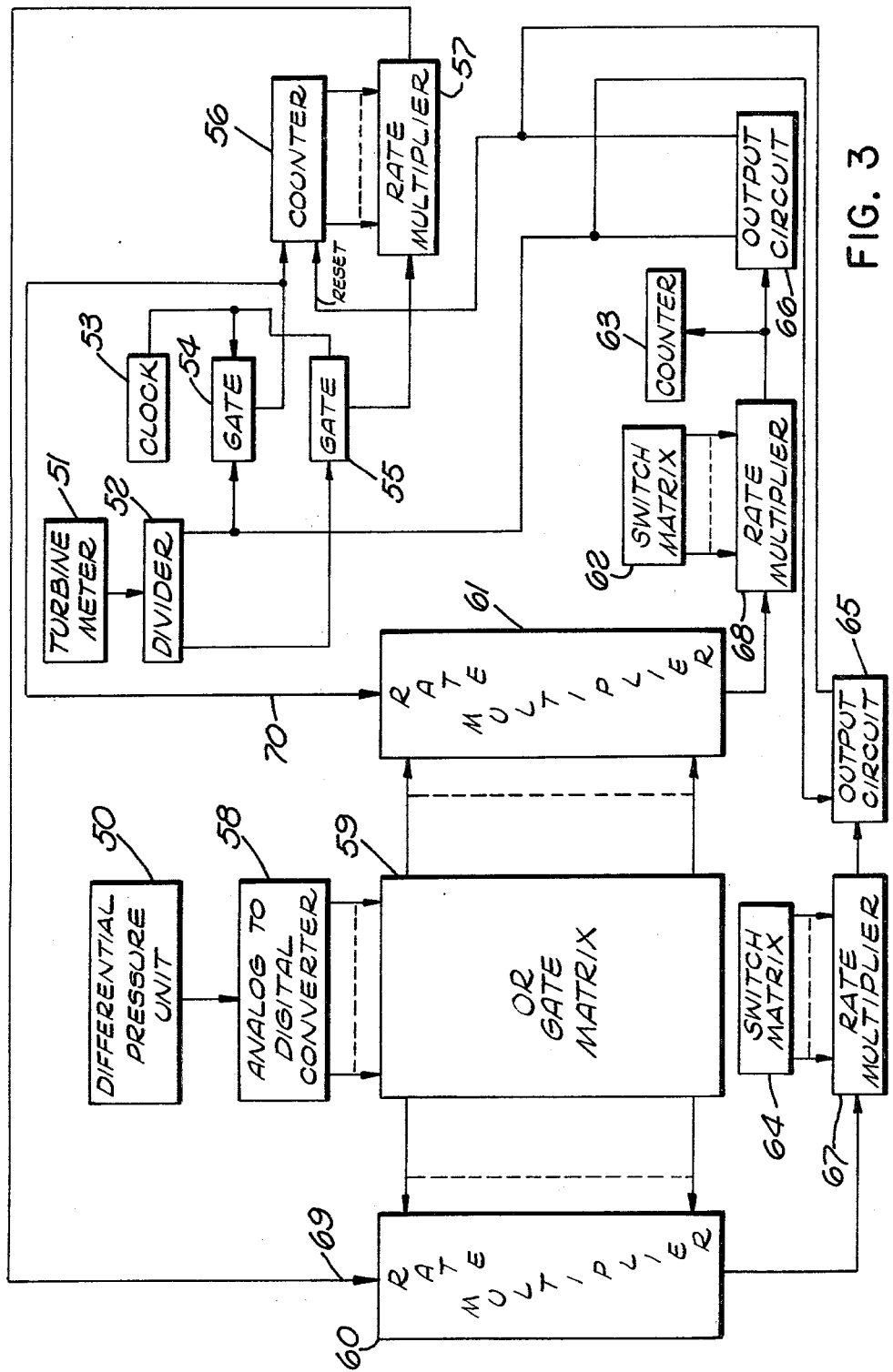
FIG. 3 is a block diagram of an alternative embodiment of the present invention.

Each individual block shown in FIGS. 1, 2, and 3 may be entirely conventional although the combination thereof is not. Moreover, output circuit 43 in FIG. 2 may be a conventional updating counter. Counter 44 counts the output of rate multiplier 42 and is reset at the beginning of the output pulse on lead 49 by multivibrator 47. Differentiator 48 transfers the contents of counter 44 to storage register 46 prior to reset of counter 44 via gating matrix 45. Differentiator 48 also resets counter 30.

When switch pole 36 is moved to engage contact 34, the number of pulses exiting gate 27 is proportional to $T_1$ and the output of each of rate multipliers 24 and 42 is proportional to $T_1\Delta p$ or $$\frac{\Delta p}{f_1} \qquad (23)$$

and is therefore proportional to mass flow rate. See equation (9).

THE EMBODIMENT OF FIG. 3

Although density, mass flow rate and total mass flow may be derived. Only one of these three properties may be derived by a single system, if desired. Any two or all three of these three properties may be derived alternatively with switches or the like. Still further, any two or all three of these three properties may be obtained simultaneously. All possible combinations or single property systems have not been disclosed herein because they will be obvious to anyone ordinarily skilled in the art to which the present invention pertains.

Notwithstanding the foregoing certain ones of said single systems and combinations may be briefly described as follows:

For density only lead 40 may be jumpered to lead 25, switch 35 omitted, and the connection from junction 33 to contact 34 omitted in FIG. 2.

For mass flow rate only, junction 33 may be jumpered to lead 25, and switch 35, gate 28, counter 30 and rate multiplier 31 with output lead 40 all omitted.

In additional counter with a switch matrix and rate multiplier may be connected to the output lead 42' of rate multiplier 42 to indicate total mass flow with or without the alternative density and with or without output circuit 43, respectively. For total mass flow, the position of pole 36 in engagement with contact 34 is used.

Any combination of density, mass flow rate and total mass flow may be indicated simultaneously as shown in FIG. 3.

In FIG. 3, DPU 50, ADC 58, turbine meter 51, divider 52, clock 53, gate 54, gate 55, counter 56 and rate multiplier 57 may be identical to, in FIG. 2, to DPU 12", ADC 23, turbine meter 13", divider 26, clock 29, gate 27, gate 28, counter 30 and rate multiplier 31, respectively. An OR gate matrix 59 supplies Δp, in FIG. 3, to both of two rate multipliers 60 and 61 for $T_1^2 \Delta p$ and $T_1 \Delta p$ multiplication, respectively.

Switch matrices 41 and 62 in FIGS. 2 and 3, respectively may be changed to cause total mass counters (none in FIG. 2 but counter 63 in FIG. 3) to produce a desired indication of total mass flow in conventional units or mass flow rate units, and vice versa.

Switch matrix 64 in FIG. 3 provides a constant multiplication for a convenient display in conventional density units in output circuit 65. All switch matrices are manually adjustable. Output circuit 65 in FIG. 3 may be identical to output circuit 43 in FIG. 2. Likewise, output circuit 66 in FIG. 3 may be identical to output circuit 43 in FIG. 2.

Switch matrix 64 in FIG. 3 is connected to a rate multiplier 67. Similarly, a rate multiplier 68 is connected from switch matrix 62.

If desired, an indicator may be included in or connected from counter 63 in FIG. 3. An additional switch matrix and rate multiplier may be connected to counter 63, if desired.

OPERATION OF THE EMBODIMENT OF FIG. 3

Counter 63 indicates total mass flow. Output circuits 65 and 66 indicate density and mass flow rate, respectively. All three of these fluid properties may be indicated simultaneously or mass flow rate and total mass flow alternately with density.

The input to rate multiplier 60 over lead 69 is proportional to $T_1^2$ as before. The input to rate multiplier 61 over lead 70 is proportional to $T_1$. Thus, the outputs of rate multipliers 67 and 68 are proportional to $T_1^2 \Delta p$ and $T_1 \Delta p$, respectively, with constants applied by switch matrices 64 and 62, respectively.

If desired, for simultaneous reading of total mass flow and mass flow rate in conventional units, the output of rate multiplier 61 may be connected to two rate multipliers and corresponding switch matrices similar to 68 and 62 connected to counter 63 and to output circuit 66, respectively, to cause counter 63 and output circuit 66 to indicate accurately, and simultaneously in conventional units, total mass flow and mass flow rate, respectively. Switch matrix 62 alone, on the other hand, may be adjusted for total mass flow or mass flow rate alternately.

Although indicators have been described, note will be taken that all outputs may be used with or without an indicator, in or without a process controller, or otherwise.

What is claimed is:

1. Fluid detection apparatus comprising: a pipe section; an orifice plate fixed in said pipe section; first means connected through said pipe section on opposite sides of said orifice plate to produce an output Δp proportional to the difference between the pressures on opposite sides of said orifice plate; a turbine meter having connections through said pipe section on opposite sides of said orifice plate, said turbine meter producing pulses at a frequency $f_1$ proportional to the volume flow rate of a fluid flowing therethrough; and second means for producing an output proportional to the ratio $$\Delta p / f_1^n$$

where n is one of the integers 1 and 2, and said ratio is proportional to a property of said fluid in said pipe section.

2. The invention as defined in claim 1, wherein $$n = 1$$

3. The invention as defined in claim 2, wherein said ratio is directly proportional to the mass flow rate of said fluid through said pipe section.

4. The invention as defined in claim 3, wherein said first means output is an electrical signal, and third means are connected from said second means, said third means including an indicator calibrated in mass per unit time.

5. The invention as defined in claim 3, including third means connected from second means to produce a signal proportional to the product of said ratio and real time.

6. The invention as defined in claim 5, including fourth means connected from said third means to indicate said product, said fourth means indicating flow in units of mass.

7. The invention as defined in claim 1, wherein $$n = 2$$

8. The invention as defined in claim 7, wherein said ratio is directly proportional to the density of said fluid.

9. The invention as defined in claim 8, wherein said first means output is an electrical signal, and third means connected from said second means, said third means including an indicator calibrated in mass per unit volume.

* * * * *